United States Patent [19]

Shepherd, Jr.

[11] Patent Number: 4,499,290

[45] Date of Patent: Feb. 12, 1985

[54] CAGED COMPOUNDS AND THEIR SYNTHESIS

[75] Inventor: Lawrence H. Shepherd, Jr., Baton Rouge, La.

[73] Assignee: Ethyl Corporation, Richmond, Va.

[21] Appl. No.: 544,517

[22] Filed: Oct. 24, 1983

[51] Int. Cl.$^3$ ............................................. C07D 313/20
[52] U.S. Cl. .................................. 549/354; 252/522 R
[58] Field of Search ................................ 549/383, 354

[56] References Cited

U.S. PATENT DOCUMENTS 3,801,600  4/1974  Naegeli ........................... 252/522 R Primary Examiner—Nicky Chan
Attorney, Agent, or Firm—Donald L. Johnson; John F. Sieberth

[57] ABSTRACT 10-oxytetracyclo[4.2.1.2$^{3,8}$.0$^{2,5}$]undecane and its lower alkyl-substituted congeners and their synthesis by contacting a tricyclo[4.2.1.0$^{2,5}$.0]non-7-en-3-yl-methanol with a strong acid so that cyclization occurs. The compounds of this invention have desirable fragrance characteristics and their stability against oxidative deterioration during storage, transportation, and use enhances their usefulness as fragrance materials.

2 Claims, No Drawings

CAGED COMPOUNDS AND THEIR SYNTHESIS

This invention provides 10-oxatetracyclo[4.2.1.2$^{3,8}$.0$^{2,5}$]undecane and its alkyl-substituted derivatiives. It also provides a process for the synthesis of such polycyclic caged compounds.

The compounds of this invention may be depicted by the formula:

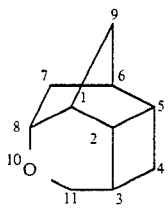

The alkyl-substituted derivatives will have one or more alkyl groups, usually lower alkyl groups (e.g., C$_{1-6}$) in any suitable position(s). Such compounds as 10-oxatetracyclo[4.2.1.2$^{3,8}$.0$^{2,5}$]undecane
3-methyl-10-oxatetracyclo[4.2.1.2$^{3,8}$.0$^{2,5}$]undecane
4-methyl-10-oxatetracyclo[4.2.1.2$^{3,8}$.0$^{2,5}$]undecane
7-methyl-10-oxatetracyclo[4.2.1.2$^{3,8}$.0$^{2,5}$]undecane
9-methyl-10-oxatetracyclo[4.2.1.2$^{3,8}$.0$^{2,5}$]undecane
4,9-dimethyl-10-oxatetracyclo[4.2.1.2$^{3,8}$.0$^{2,5}$]undecane
9,9-dimethyl-10-oxatetracyclo[4.2.1.2$^{3,8}$.0$^{2,5}$]undecane
1,4,6-trimethyl-10-oxatetracyclo[4.2.1.2$^{3,8}$.0$^{2,5}$]undecane are exemplary.

The compounds of this invention are produced by contacting a tricyclo[4.2.1.0$^{2,5}$]non-7-en-3-yl-methanol (synthesis of which is described in U.S. Pat. No. 3,810,949) with a strong acid such as phosphoric acid, polyphosphoric acid, benzene sulfonic acid, toluene sulfonic acid, HCl, H$_2$SO$_4$, and the like. This results in the cyclization yielding the compounds of this invention.

Since the cyclization proceeds via protonation of a double bond, any strong acid may be used provided of course that it does not destroy the tricyclo[4.2.1.0$^{2,5}$]non-7-en-3-yl-methanol being used in the process. Phosphoric acid is preferred because of its availability and good reactivity in the process.

The process is relatively facile and thus is ordinarily conducted under mild temperature conditions. If desired, mildly elevated temperatures (e.g., up to about 100° C. or above) may be used in order to enhance reaction rate. Conversely, it is possible to perform the cyclization at temperatures below room temperature (e.g., as low as about 0° C. or below). For best results, the acid and the tricyclo[4.2.1.0$^{2,5}$]non-7-en-3-yl-methanol should be mixed or agitated such as by stirring or shaking. Naturally, the system should be allowed to interact for a sufficient period for the cyclization reaction to take place. Thus except for using a temperature at which the reaction proceeds at a satisfactory reaction rate, the reaction conditions for the process are not of particular importance.

The following example illustrates the invention:

EXAMPLE

A sample of tricyclo[4.2.1.0$^{2,5}$]non-7-en-3-yl-methanol (5.88 g, 39 mmoles) was dissolved in 20 mL of 85% orthophosphoric acid (H$_3$PO$_4$) and heated on a steam bath for three hours at about 90° C. At the end of this period, the sample was cooled to room temperature and poured into 50 mL of water. The resulting aqueous mixture was extracted three times with 25-mL portions of diethyl ether. The ether extracts were combined and washed once with 25 mL of dilute aqueous NaHCO$_3$ in order to remove residual traces of acid. The ether layer was then dried over anhydrous MgSO$_4$, filtered and evaporated on a steam bath. The resulting colorless mobile liquid was distilled at 91.5°–92.5° C. (13.5–14 mm Hg). A total of 1.70 grams (11.3 mmoles, 29% yield) distilled product was collected. NMR and IR analyses showed that the product was completely saturated (no olefinic bonds) and no hydroxyl group was present. Mass spectral analyses showed that the product retained the same molecular composition as the starting material (C$_{10}$H$_{14}$O) which is consistent with the structure 10-oxatetracyclo[4.2.1.2$^{3,8}$.0$^{2,5}$]undecane.

In like manner, 4-ethyl-10-oxatetracyclo[4.2.1.2$^{3,8}$.0$^{2,5}$]undecane can be formed from 4-ethyl-tricyclo[4.2.1.0$^{2,5}$]non-7-en-3-yl-methanol, 1,6-dimethyl-10-oxatetracyclo[4.2.1.2$^{3,8}$.0$^{2,5}$]undecane can be formed from 1,6-dimethyl-tricyclo[4.2.1.0$^{2,5}$]non-7-en-3-yl-methanol, and so forth.

The compounds of this invention have desirable fragrance characteristics and thus may be used as perfumes or odorants in a variety of products, such as sanitizing solutions, kitchen and bathroom cleansers, furniture polishes, laundry detergents, wax candles, and like scented products. Their stability against oxidative deterioration during storage, transportation, and use enhances their usefulness as fragrance materials.

It is to be understood and appreciated that although a three-dimensional molecular structure has been depicted in this description of the invention, it is not intended that the invention be limited to any given geometric or stereo configuration. The three-dimensional formula has been utilized simply as a convenient way of depicting the complex caged polycyclic compounds of this invention.

I claim:

1. 10-oxatetracyclo[4.2.1.2$^{3,8}$.0$^{2,5}$]undecane or its lower alkyl-substituted congeners.

2. 10-oxatetracyclo[4.2.1.2$^{3,8}$.0$^{2,5}$]undecane, a compound of claim 1.

* * * * *